(12) United States Patent
Tsai et al.

(10) Patent No.: US 10,874,368 B2
(45) Date of Patent: Dec. 29, 2020

(54) SCANNING IMAGING DEVICE AND ANIMAL CARRYING BED THEREOF

(71) Applicant: DELTA ELECTRONICS, INC., Taoyuan (TW)

(72) Inventors: Yi-Da Tsai, Taoyuan (TW); Chih-Yuan Hsu, Taoyuan (TW)

(73) Assignee: DELTA ELECTRONICS, INC., Taoyuan (TW)

( * ) Notice: Subject to any disclaimer, the term of this patent is extended or adjusted under 35 U.S.C. 154(b) by 531 days.

(21) Appl. No.: 15/870,897

(22) Filed: Jan. 13, 2018

(65) Prior Publication Data

US 2018/0214108 A1   Aug. 2, 2018

Related U.S. Application Data

(60) Provisional application No. 62/448,522, filed on Jan. 20, 2017.

(30) Foreign Application Priority Data

Dec. 15, 2017   (TW) .............................. 106144068 A

(51) Int. Cl.
    *A61B 6/00*       (2006.01)
    *A61D 7/04*       (2006.01)
    (Continued)

(52) U.S. Cl.
    CPC ............ *A61B 6/508* (2013.01); *A61B 5/0555* (2013.01); *A61B 5/70* (2013.01); *A61B 6/0407* (2013.01);
    (Continued)

(58) Field of Classification Search
    CPC ......... A61B 6/508; A61B 5/70; A61B 6/0407; A61B 5/0555; A61B 6/0428; A61B 6/03; A61B 6/04; A61D 7/04; A61D 3/00; A61M 16/00; A61M 16/125; A61M 2250/00; A61M 16/0891; A61M 16/1075
    See application file for complete search history.

(56) References Cited

U.S. PATENT DOCUMENTS 8,334,698 B2 * 12/2012 Tammer ............... A61B 5/0555
                                              324/321
8,482,278 B2 *  7/2013 Wolke ................. G01R 33/307
                                              324/307

(Continued)

FOREIGN PATENT DOCUMENTS

WO    WO-9428431 A1 * 12/1994  ............. G01R 33/30

*Primary Examiner* — Hien N Nguyen
(74) *Attorney, Agent, or Firm* — Hauptman Ham, LLP

(57) ABSTRACT

An animal carrying bed includes a tubular unit, an electrical connector and an end cover unit. The electrical connector is arranged on one end of the tubular unit, and the end cover unit is arranged at another end thereof. The end cover unit is formed of an intake channel and a discharge channel therein and separated from each other. The end cover unit is formed of an intake opening inside the tubular unit and connected to the intake channel. The end cover unit is formed of a plurality of discharge openings inside the tubular unit and connected to the discharge channel. The intake channel and the discharge channel are connected to the electrical connector via guide tubes respectively, and the guide tubes are installed inside the tubular unit.

16 Claims, 5 Drawing Sheets

(51) Int. Cl.
 *A61B 5/00* (2006.01)
 *A61B 6/04* (2006.01)
 *A61M 16/00* (2006.01)
 *A61B 5/055* (2006.01)
 *A61D 3/00* (2006.01)
 *A61B 6/03* (2006.01)
 *A61M 16/12* (2006.01)
 *A61M 16/08* (2006.01)
 *A61M 16/10* (2006.01)

(52) U.S. Cl.
 CPC .............. *A61B 6/0428* (2013.01); *A61D 3/00* (2013.01); *A61D 7/04* (2013.01); *A61M 16/00* (2013.01); *A61B 6/03* (2013.01); *A61B 6/04* (2013.01); *A61M 16/0891* (2014.02); *A61M 16/1075* (2013.01); *A61M 16/125* (2014.02); *A61M 2250/00* (2013.01)

(56) References Cited

U.S. PATENT DOCUMENTS

| | | | | |
|---|---|---|---|---|
| 8,774,899 B2* | 7/2014 | Chiodo | ................. | A61B 6/508 600/415 |
| 2001/0053878 A1* | 12/2001 | Ferris | ................... | A61B 5/0555 600/415 |
| 2008/0072836 A1* | 3/2008 | Chiodo | ............... | A01K 1/0613 119/417 |
| 2010/0269260 A1* | 10/2010 | Lanz | ................... | A61B 5/0555 5/601 |
| 2017/0035982 A1* | 2/2017 | Roseman | .............. | A61M 16/01 |

\* cited by examiner

SCANNING IMAGING DEVICE AND ANIMAL CARRYING BED THEREOF

BACKGROUND OF THE INVENTION

Field of the Invention

The technical field relates to a scanning imaging device, in particular, to a scanning image device for animals and an animal carrying bed thereof.

Description of Related Art

Currently existing scanning image devices, such as, X ray, computed tomography (CT), magnetic resonance imaging (MRI) or positron emission tomography (PET) etc., typically comprise a machine unit for scanning animals, and the machine unit is installed with a moveable carrying platform having a carrying bed arranged thereon. The internal of the carrying bed is formed of a chamber for receiving an animal therein. The carrying platform is able to move the carrying bed into the machine unit for scanning the animal on the bed. Since the animal needs to be sedated in order to perform the scanning, typically, the method of gas Anesthesia is used by injecting Anesthesia gas into the chamber of the carrying bed for the animal inside the chamber to inhale such gas. To control the Anesthesia process, typically, a mask is used to cover the nose and mouth of the animal, followed by providing the Anesthesia gas into the mask, in general, one end of the carrying bed is arranged to face toward the machine unit, and such end enters into the machine unit first; whereas the Anesthesia gas source is externally connected to the other end of the carrying bed in order to prevent interface with of the carrying bed actuation due to the external tubes and wires. However, with such design, the animal is secured onto the carrying bed at the external connection end of the Anesthesia gas source such that the carrying bed need be completely conveyed into the machine unit in order to move the animal to the scanning area, and a great portion of the moving mechanism needs to be extended into the machine, making the mechanical design to be difficult. Furthermore, the carrying bed is further externally connected to a heating source. The heating source is arranged adjacent to the Anesthesia gas source in order to allow the Anesthesia gas to mix with the heated source order to change the concentration thereof.

In view of the above, the inventor seeks to overcome the aforementioned drawbacks, and after years of researches along with the utilization of scientific principles, the inventor provides a novel design of the present invention in order to overcome the aforementioned drawbacks.

SUMMARY OF THE INVENTION

The present invention is related to a scanning imaging device for animal and an animal carrying bed thereof.

The present invention provides an animal carrying bed, comprising: a tubular unit, an electrical connector and an end cover unit. The electrical connector is arranged at one end of the tubular unit and the end cover unit is arranged at another end of the tubular unit. The end cover unit includes an intake channel and a discharge channel arranged therein and spaced apart from each other. The end cover unit includes an intake opening formed inside the tubular unit and connected to the intake channel. The end cover unit includes a plurality of discharge openings formed inside the tubular unit and connected to the discharge channel. The intake channel and the discharge channel are connected to the electrical connector via a guide tube, and the guide tube is arranged inside the tubular unit.

According to an embodiment of the animal carrying bed of the present invention, the tubular unit comprises a semi-tubular member and an arched cover member covering onto the semi-tubular member, and the arched cover member is locked onto the end cover unit. The animal carrying bed of the present invention further comprises a carrying board installed inside the tubular unit, and at least a portion of the carrying board is arranged corresponding to a conical tube.

According to an embodiment of the animal carrying bed of the present invention, it further comprises a conical tube arranged inside the tubular unit, and a conical tip of the conical tube is connected to the intake opening and the discharge openings are arranged outside of the conical tube.

According to an embodiment of the animal carrying bed of the present invention, the end cover unit comprises a first cover member and a second cover member stacked onto each other. The intake channel is formed on the first cover member, and the discharge channel is formed on the second cover member. The first cover member covers onto the discharge channel, and the second cover member covers onto the intake channel. The end cover unit is of a plate shape and receives the intake channel and the discharge channel therein. In addition, the discharge channel surrounds the intake channel. The first cover member is exposed out of the tubular unit, and the second cover member is received inside the tubular unit. The intake opening and the discharge openings are formed on the second cover member. The discharge openings are arranged to surround the intake opening. The tubular unit comprises a semi-tubular member and an arched cover member covers onto the semi-tubular member. The arched cover member is locked onto the first cover member. The end cover unit includes a plurality of exchange openings formed thereon, and each one of the exchange openings is connected to inner and outer sides of the tubular unit. In addition, each one of the exchange openings penetrates through the first cover member and the second cover member.

According to an embodiment of the animal carrying bed of the present invention, the electrical connector includes a heated air outlet arranged to face toward an internal of the tubular unit.

The present invention further provides a scanning imaging device, comprising a machine unit, and the machine unit includes an entrance. The entrance includes a carrying platform arranged at an external of the entrance. The carrying platform is connected to the electrical connector of the aforementioned animal carrying bed, and one end the tubular member installed with the end cover unit thereon is arranged to face toward the entrance. In addition, the machine unit includes a sliding track, and the sliding track is arranged horizontally. The carrying platform is disposed on the sliding track and is configured to move along the sliding track in order to move the animal carrying bed into the machine unit. The machine unit includes a protruding platform extended outward from the entrance. The sliding track is installed on the protruding platform and extends into the entrance.

For the scanning imaging device and the animal carrying bed of the present invention, the intake opening uses the end cover unit to install at the other end of the tubular unit opposite from the electrical connector; therefore, during the use of the scanning imaging device, the animal is secured onto one end of the tubular unit having the end cover unit thereon. Since such end is moved into the machine unit first, the animal is secured onto this end and it only requires to move a portion of the animal carrying bed into the machine; consequently, the mechanical structure can be simplified. The discharge opening is configured to surround the intake opening in order to properly collect the remaining Anesthesia gas from all directions such that it is able to prevent Anesthesia gas from dissipating into the tubular unit. By separating the intake opening and the discharge opening with the conical tube, the Anesthesia gas can be properly guided into the nose of the animal in order to prevent the situation where the Anesthesia gas is not inhaled by the animal but discharged out of the unit. Furthermore, the intake opening and the heated air outlet are respectively arranged at two ends of the tubular unit such that it is able to prevent changes of the concentration during the mixing of Anesthesia gas and heated air. Moreover, the scanning imaging device and animal carrying bed of the present invention utilize the end cover unit to construct the intake channel and the discharge channel; therefore, the volume of the animal carrying bed can be reduced.

DETAILED DESCRIPTION OF THE INVENTION

Figure 1:
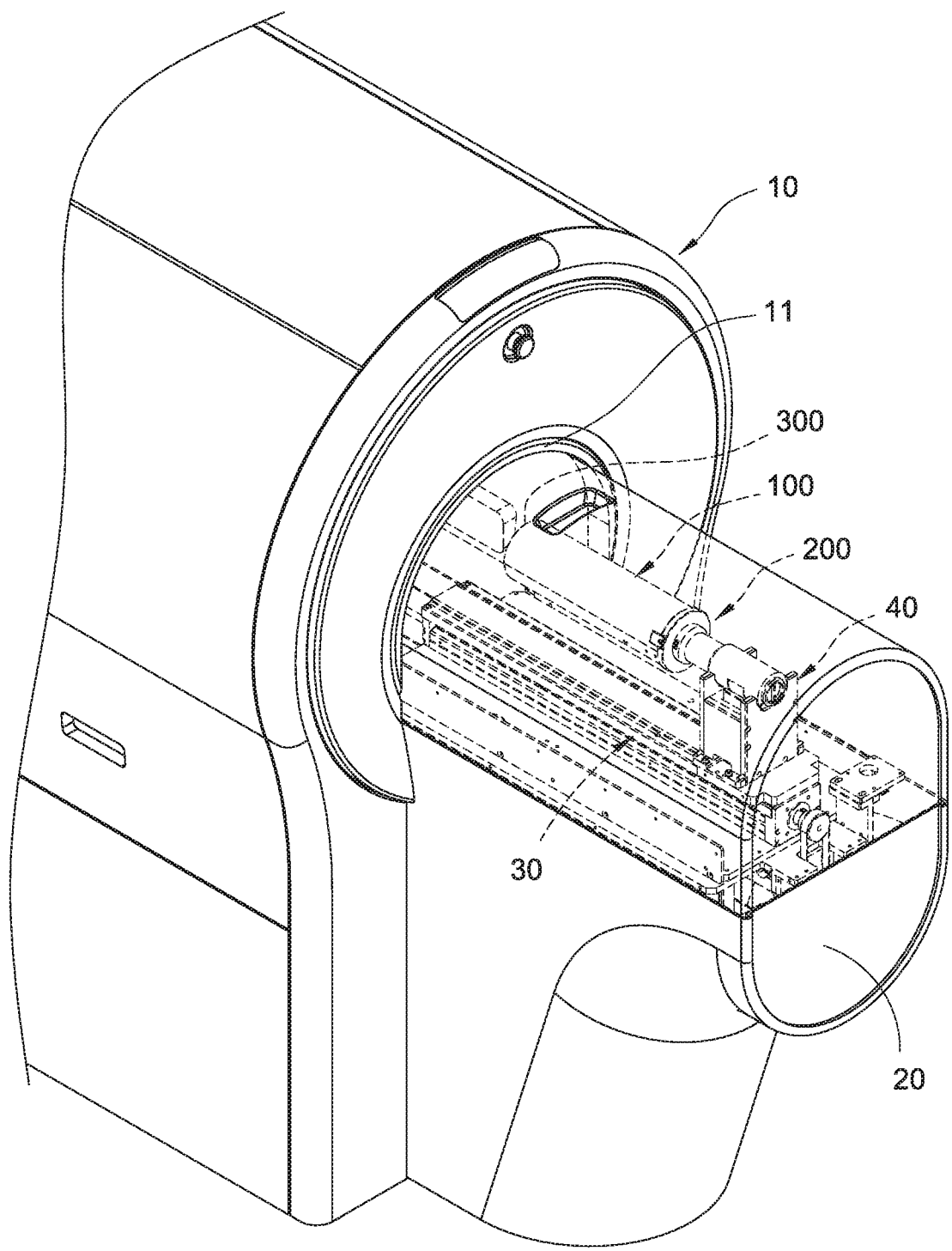
FIG. 1 is a perspective view of the scanning imaging device of the present invention.
Figure 2:
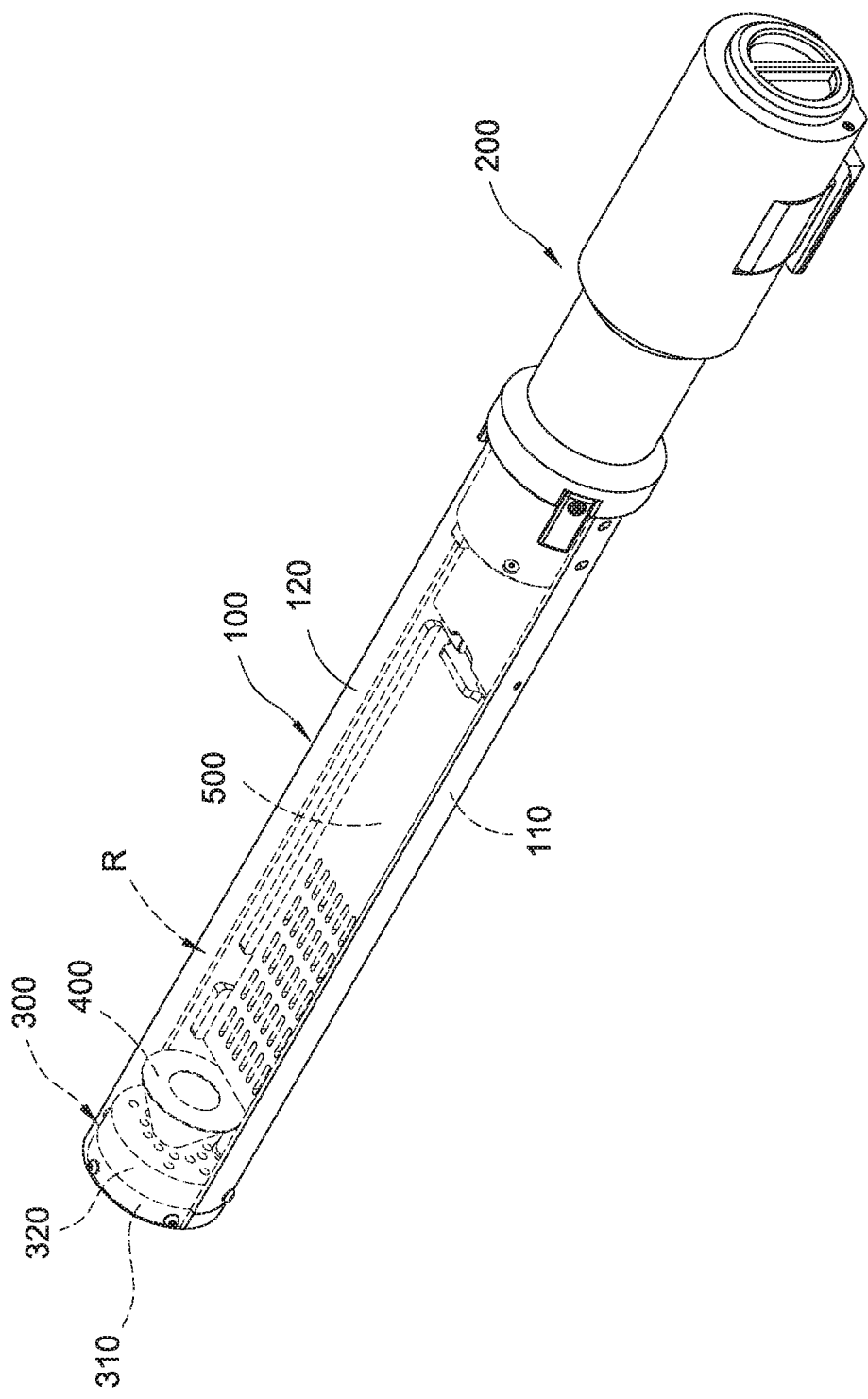
FIG. 2 is a perspective view of the animal carrying bed of the present invention.
Figure 3:
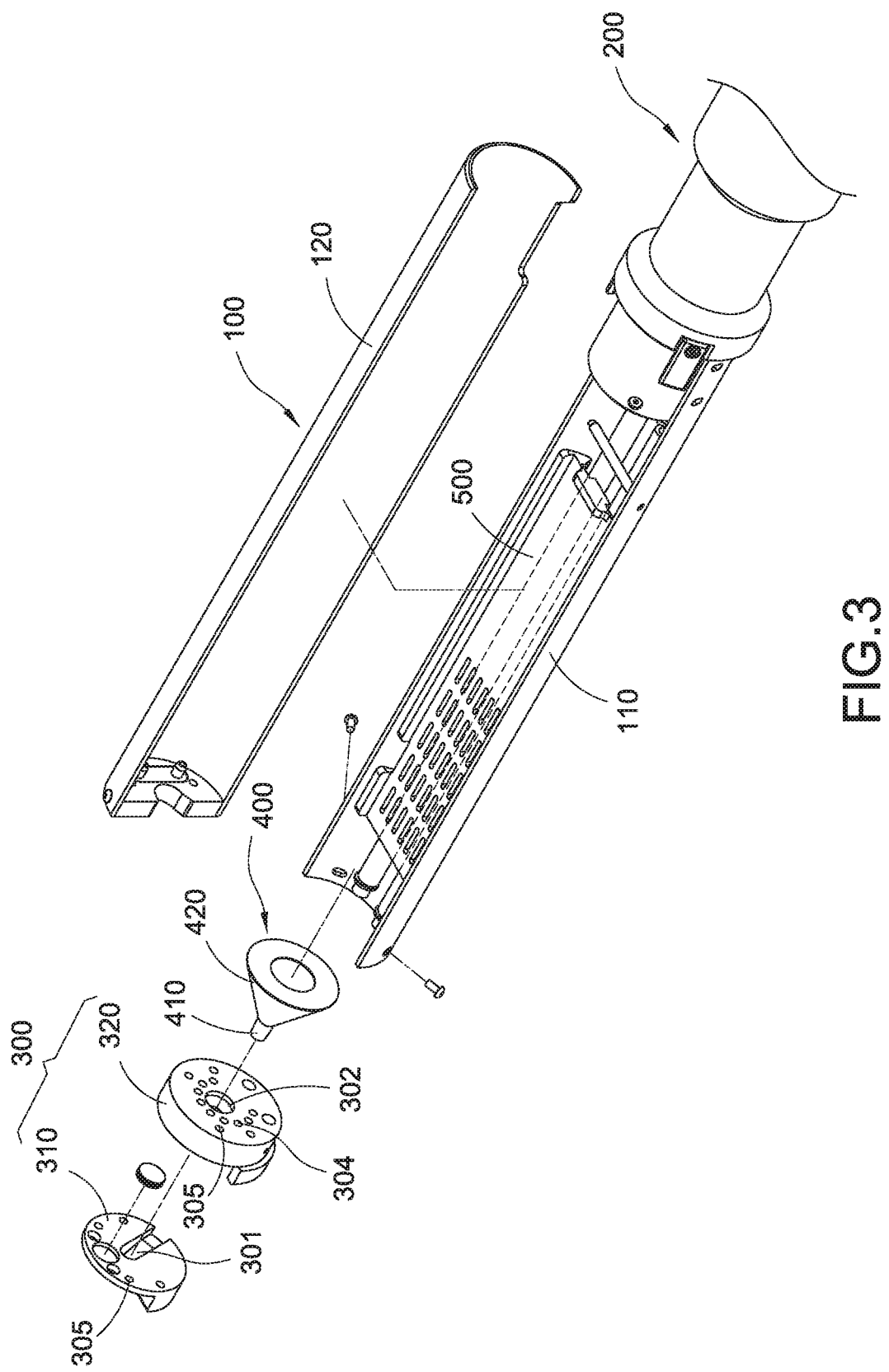
FIG. 3 shows a perspective exploded view of the animal bed of the present invention.
Figure 4:
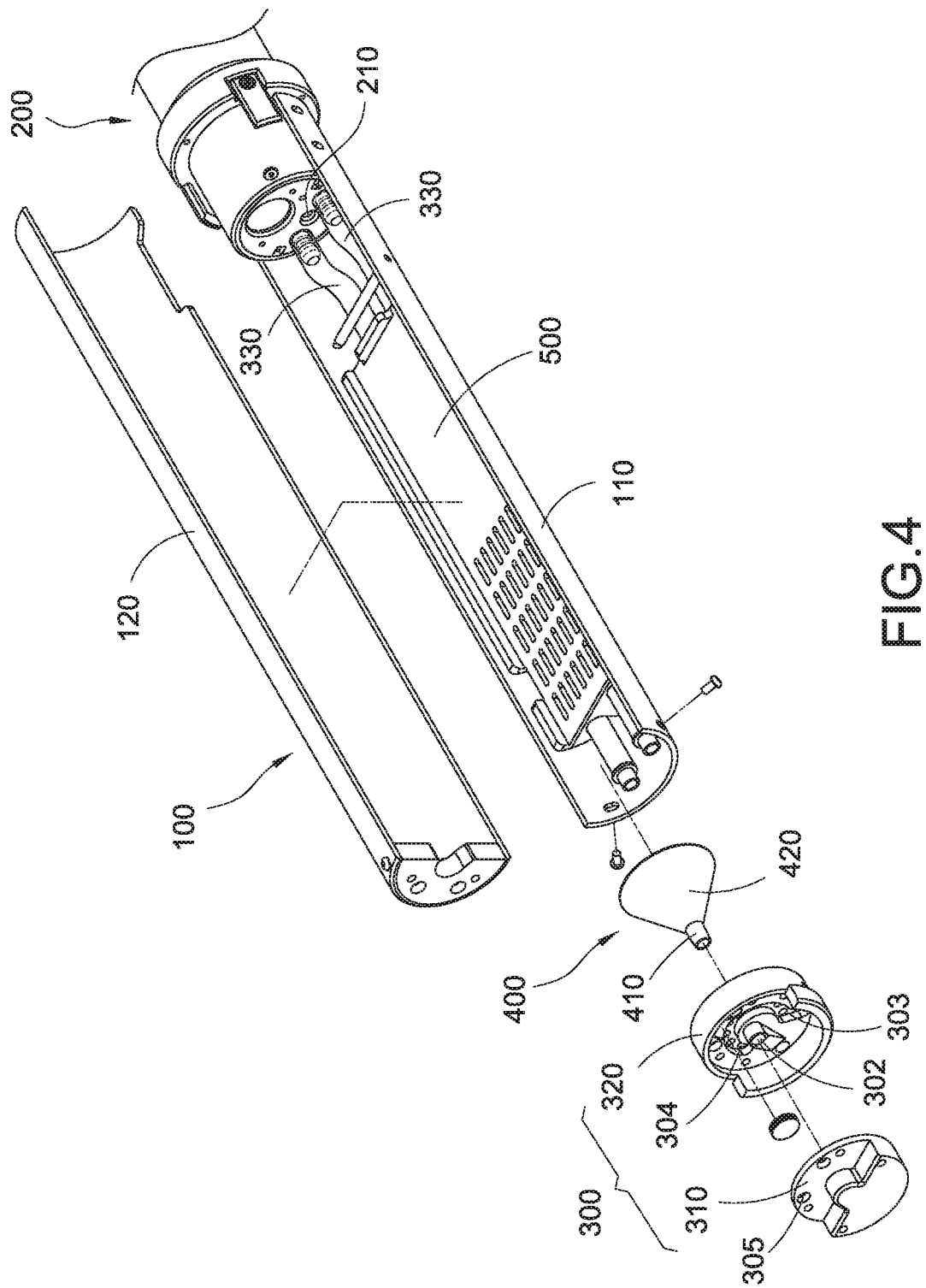
FIG. 4 shows another perspective exploded view of the animal bed of the present invention.
Figure 5:
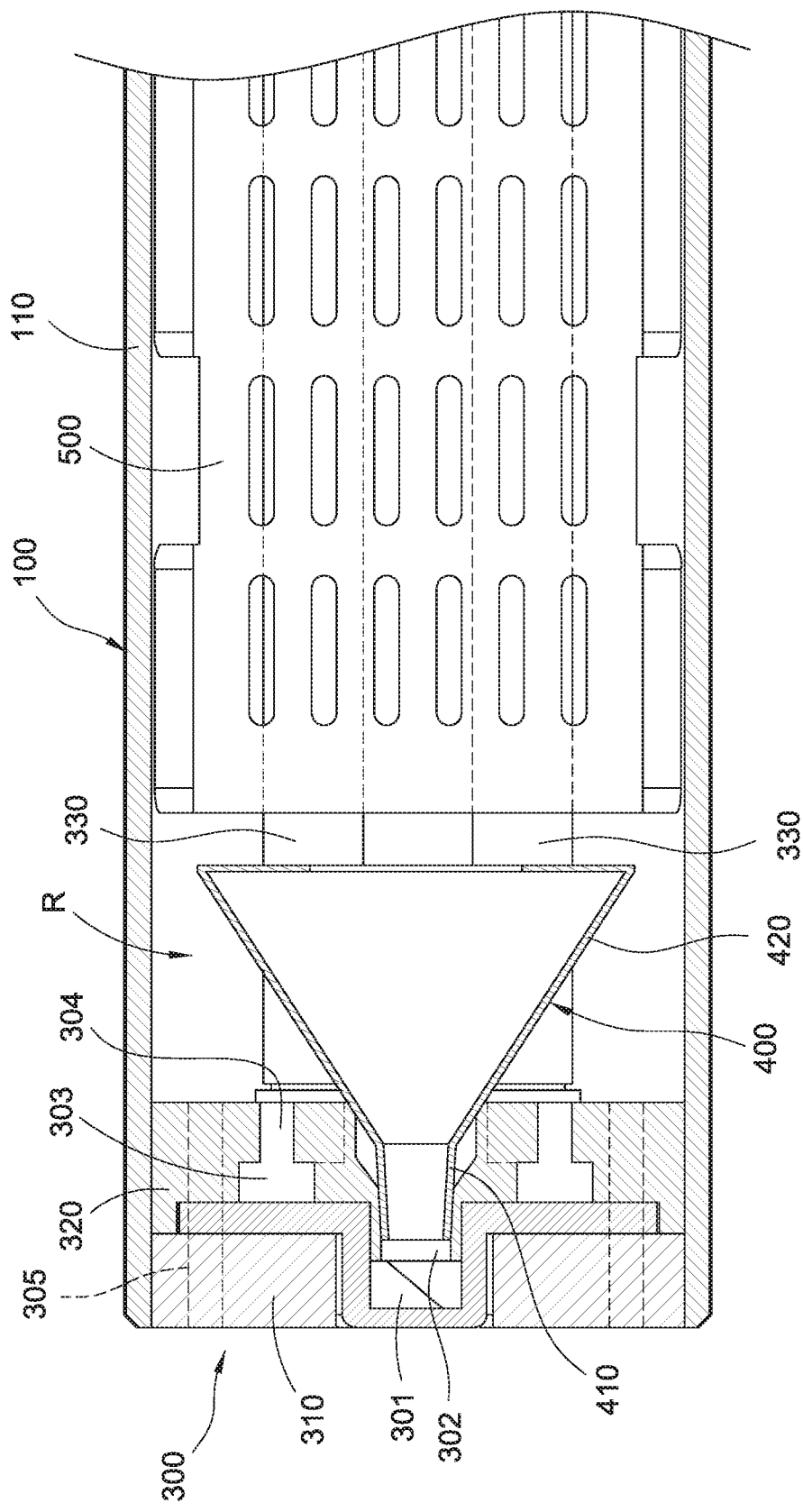
FIG. 5 is a partial schematic view of the animal carrying bed of the present invention.

As shown in FIG. 1, according to an exemplary preferred embodiment of the present invention, a scanning imaging device is provided. The scanning imaging device comprises a machine unit 10 for scanning an animal. The machine unit 10 includes an entrance 11 and a protruding platform 20 extended outward from the entrance 11. The protruding platform 20 includes a sliding track 30 thereon, and the sliding track 30 is arranged horizontally. In addition, the sliding track 30 extends into the entrance 11. The sliding track 30 further includes a carrying platform 40 arranged thereon, and the carrying platform 40 is located at an external of the entrance 11 and is used for connecting to an animal carrying bed. Furthermore, the carrying platform is configured to move along with the sliding track 30.

As shown in FIG. 1 to FIG. 5, the animal carrying bed comprises a tubular unit 100, an electrical connector 200 arranged at one end of the tubular unit 100, an end cover unit 300 arranged at another end of the tubular unit 100, an inner conical tube 400 installed inside the tubular unit 100 and a carrying board 500 installed inside the tubular unit 100. The two ends of the tubular unit 100 are respectively locked and connected to the electrical connector 200 and the end cover unit 300 in order to form a receiving space R. The electrical connector 200 is connected to the carrying platform 40, and one end of the tubular unit 100 having the end cover unit 300 installed thereon is configured to face toward the entrance 11. The carrying platform 40 is able to move along the sliding track 30 in order to convey the animal carrying bed into the machine unit 10 from the entrance 11. The specific description of the structure of the animal carrying bed of the present invention is provided in the following.

The tubular unit 100 comprises a semi-tubular member 110 and an arched cover member 120. The arched cover member 120 covers onto the opening side of the semi-tubular member 110 in order to close and open with the semi-tubular member 110 such that the tubular unit 100 is constructed. In addition, the arched cover member 120 can be, preferably, locked onto the end cover unit 300 in order to be secured and attached onto the semi-tubular member 110. However, the present invention is not limited to the form of the tubular unit; for example, the tubular unit 100 can also be an integrally formed tubular unit, and the two ends of the tubular unit 100 can be locked the electrical connector 200 and the end cover unit 300 respectively.

The electrical connector 200 is used for connecting with the carrying platform 40 of the scanning imaging device and is electrically connected to the machine unit 10 via the carrying platform 40. In addition, the electrical connector 200 is connected to a positive pressure gas source and a negative pressure gas source for the Anesthesia gas respectively; therefore, the electrical connector 200 is able to supply and discharge the Anesthesia gas inside the tubular unit 100. The electrical connector 200 is further connected to a heated air source, and the electrical connector 200 includes a heated air outlet 210 configured to face toward the internal of the tubular unit 100; therefore, the electrical connector 20 is able to supply heated air to the internal of the tubular unit 100 via the heated air outlet 210.

The end cover unit 300 is of a plate shape or a circular disk shape, and its internal includes the intake channel 301 and discharge channel 303 formed there on and separated from each other (isolated and unconnected). The end cover unit 300 includes an intake opening 302 located inside the tubular unit 100 and connected to the intake channel 301 and a plurality of discharge openings 304 located inside the tubular unit 100 and connected to the discharge channel 303. The intake channel 301 and the discharge channel 303 are respectively connected to the electrical connector 200 via the guide tube 330, and the guide tube 330 is arranged inside the tubular unit 100. The construction methods of the intake channel 301 and the discharge channel 303 are described in detail as follows. In an exemplary embodiment of the present invention, the end cover unit 300, preferably, comprises a first cover member 310 and a second cover member 320. The first cover member 310 and the second cover member 320 are both of plate shapes and configured to stack onto each other. The first cover member 310 is exposed out of the tubular unit 100, the second cover member 320 is received inside the tubular unit 100, and the arched cover 120 is, preferably, locked onto the first cover member 310. When the first cover member 310 and the second cover member 320 are separated from each other, the intake channel 301 forms a slot indented into the surface of the first cover member 310, and the discharge channel 303 forms a slot indented into the surface of the second cover member 320. When the first cover member 310 and the second cover member 320 are stacked onto each other to form the end cover unit 300, the second cover 320 covers the intake channel 301 to seal the intake channel 301 in order to form the channel inside the end cover unit 300. In addition, the first cover member 310 covers the discharge channel 303 to seal the discharge channel 303 in order to form the channel inside the end cover unit 300. In an exemplary embodiment of the present invention, the discharge channel is configured to surround the intake channel 301, and the intake opening 302 and the discharge openings 304 are formed on the second cover member 320, and facing toward one identical side inside the tubular unit 100; moreover, the discharge openings 304 are arranged to surround the intake opening 302. In another exemplary embodiment, the end cover unit 300 can also be integrally formed to have a plate shape. In view of the above, the plate shape structure of the end cover unit 300 is able to significantly reduce the volume of the animal carrying bed in order to prevent occupying the internal space of the machine 10, thereby reducing the volume of the machine 10.

The conical tube 400 includes one end tapered into a conical tip 410, and another end of the conical tube is an expansion end 420 opposite from the conical tip 410. In addition, the conical tube 400 expands from the conical tip 410 toward the expansion end 420. The conical tip 410 is connected to the intake opening 302 and the discharge openings 304 are located outside the conical tube 400.

At least a portion of the carrying board 500 is arranged corresponding to the conical tube 400. In an exemplary embodiment of the present invention, the carrying board 500 is preferably of an elongated shape and is configured to extend longitudinally along the tubular unit 100. The guide tube 330 is arranged underneath the carrying board 500. One end of the carrying board 500 is arranged corresponding to the location of the conical tube 400, and it can extend to the lower portion in front of the conical tube 400. The carrying board 500 is used for carrying an animal; therefore, the conical tube 400 can cover the nose of the animal.

During the use of the scanning imaging device and the animal carrying bed of the present invention, the electrical connector 200 of the animal carrying bed is connected to the carrying platform 40 of the scanning imaging device in order to allow each guide tube 330 of the animal carrying bed to be respectively connected to the positive pressure gas source and the negative pressure gas source for providing the Anesthesia gas. The positive pressure gas source is connected to the intake channel 301 via the guide tube 330, and the negative pressure gas source is connected to the discharge channel 303 via the guide tube 330. The Anesthesia gas is supplied into the tubular unit 100 via the electrical connector 200 and is supplied into the intake channel 301 via the guide tube 330 connected inside the tubular unit 100, followed by conveying it into the intake opening 302 and further entering into the conical tip 410 of the conical tube 400 for the animal to inhale the Anesthesia gas. The remaining Anesthesia gas passing through the conical tube 400 is then delivered out of the conical tube 400 via the expansion end 420 opposite from the conical tip 410. The Anesthesia gas delivered out of the conical tube 400 passes through the discharge openings 304 surrounding the intake opening 302 in order to be sucked into the discharge channel 303, following which it then passes through the guide tube 330 connected to the internal of the tubular unit 100 for discharging out of the animal carrying bed via the electrical connector 200.

In an exemplary embodiment of the present invention, the end cover unit 300 preferably includes a plurality of exchange openings 305 formed thereon and penetrating therethrough. Each one of the exchange openings 305 is connected to the inner and outer sides of the tubular unit 100, and each one of the exchange openings 305 penetrates through the first cover member 310 and the second cover member 320 respectively. The exchange openings can be provided for natural exchange air at the inner and outer sides of the tubular unit 100, and the excessive heated air can also be discharged out of the tubular unit 100 via the exchange openings 305.

The advantages of the present invention include at least the following:

The intake opening 302 of the animal carrying bed of the present invention utilizes the end cover unit 300 to be installed on the other end of the tubular unit 100 opposite from the electrical connector 200; therefore, during the use of the scanning imaging device of the present invention, the nose and mouth of the animal can be placed at one end of the tubular unit 100 with the end cover unit 300 installed thereon. Since such end is moved into the machine unit 10 first, with the animal secured onto this end, it is only required to move a portion of the animal carrying bed into the machine unit 10. As a result, the mechanical structure thereof can be simplified.

The intake opening 302 and the discharge opening 304 are both arranged on one identical side of the end cover unit 300. In addition, they are also arranged to face toward the receiving space in the tubular unit 100 and are connected to the guide tube 330 inside the tubular unit 100. Therefore, the delivery and collection of Anesthesia gas can be completed at the internal of the animal carrying bed such that the user is only required to place the animal on the carrying platform 40 without the need to externally connect other guide tubes 330 to the animal carrying bed tubular unit 100. Consequently, the convenience of use of the device can be increased.

The discharge openings 304 are arranged to surround the intake opening 302 such that they are able to properly collect the remaining Anesthesia gas from all directions in order to prevent the Anesthesia gas from dissipating inside the tubular unit 100 or dissipating out of the tubular unit 100.

By using the conical tube 400 separating the intake opening 302 and the discharge opening 304, it is able to properly guide the Anesthesia gas to the nose of the animal in order to prevent the situation where the Anesthesia gas is being discharged out of the device without being inhaled by the animal.

Furthermore, the intake opening 302 and the heated air opening 210 are configured at two ends of the tubular unit 100 such that it is able to prevent the change of concentration during the mixing of the Anesthesia gas and the heated air.

Moreover, the scanning imaging device and the animal carrying bed of the present invention can utilize the end cover unit 300 to form the intake channel 301 and the discharge channel 303; therefore, the volume of the animal carrying bed can be reduced.

The above describes the preferable and feasible exemplary embodiments of the present invention for illustrative purposes only, which shall not be treated as limitations of the scope of the present invention. Any equivalent changes and modifications made in accordance with the scope of the claims of the present invention shall be considered to be within the scope of the claim of the present invention.

What is claimed is:

1. An animal carrying bed, comprising:
   a tubular unit adapted to carry the animal;
   an electrical connector arranged on one end of the tubular unit; and
   an end cover unit arranged on another end of the tubular unit, the end cover unit having an intake channel and a discharge channel arranged therein and separated from each other; the end cover unit having an intake opening formed inside the tubular unit and connected to the intake channel; the end cover unit having a plurality of discharge openings formed thereon inside the tubular unit and connected to the discharge channel; the intake channel and the discharge channel connected to the electrical connector via a guide tube respectively, and the guide tubes arranged inside the tubular unit.

2. The animal carrying bed according to claim 1, wherein the tubular unit comprises a semi-tubular member and an arched cover member covering onto the semi-tubular member; and the arched cover member is locked onto the end cover unit.

3. The animal carrying bed according to claim 1, further comprising a conical tube arranged inside the tubular unit; the conical tip of the conical tube is connected to the intake opening; and the discharge openings are located external of the conical tube.

4. The animal carrying bed according to claim 3, further comprising a carrying board; and at least a portion of the carrying board is arranged corresponding to the conical tube.

5. The animal carrying bed according to claim 1, wherein the end cover unit comprises a first cover member and a second cover member; the intake channel is formed on the first cover member, and the discharge channel is formed on the second cover member.

6. The animal carrying bed according to claim 5, wherein the first cover member covers the discharge channel, and the second cover member covers the intake channel.

7. The animal carrying bed according to claim 5, wherein the end cover unit is of a plate for receiving the intake channel and the discharge channel thereon; and the discharge channel surrounds the intake channel.

8. The animal carrying bed according to claim 5, wherein the first cover member is exposed out of the tubular unit, and the second cover member is received inside the tubular unit.

9. The animal carrying bed according to claim 5, wherein the intake opening and the discharge openings are formed on the second cover member.

10. The animal carrying bed according to claim 5, wherein the discharge openings are arranged to surround the intake opening.

11. The animal carrying bed according to claim 5, wherein the tubular unit comprises a semi-tubular member and an arched cover member covers the semi-tubular member; the arched cover member is locked onto the first cover member.

12. The animal carrying bed according to claim 5, wherein the end cover unit includes a plurality of exchange openings formed thereon and penetrating therethrough; each one of the exchange openings is connected to inner and outer sides of the tubular unit, and each one of the exchange openings penetrates through the first cover member and the second cover member.

13. The animal carrying bed according to claim 1, wherein the electrical connector includes a heated air outlet arranged to face toward an internal of the tubular unit.

14. A scanning imaging device, comprising a machine unit, the machine unit having an entrance and a carrying platform arranged at an external of the entrance; the carrying platform connected to the electrical connector of the animal carrying bed according to claim 1, and one end the tubular unit installed with the end cover unit thereon is arranged to face toward the entrance.

15. The scanning imaging device according to claim 14, wherein the machine unit includes a sliding track formed thereon; the sliding track is arranged horizontally, and the carrying platform is disposed on the sliding track and configured to move along the sliding track in order to move the animal carrying bed into the machine unit.

16. The scanning imaging device according to claim 15, wherein the machine unit includes a protruding platform extended outward from the entrance, and the sliding track is arranged on the protruding platform and extends into the entrance.

* * * * *